United States Patent
Xing et al.

(10) Patent No.: US 7,767,438 B2
(45) Date of Patent: Aug. 3, 2010

(54) MICROARRAY DEVICES HAVING CONTROLLABLE REACTION VOLUME

(75) Inventors: Wanli Xing, Beijing (CN); Fei Jun Xian, Beijing (CN); Xianhua Wang, Beijing (CN); Jing Cheng, Beijing (CN)

(73) Assignee: CapitalBio Corporation, Beijing (CN)

( * ) Notice: Subject to any disclaimer, the term of this patent is extended or adjusted under 35 U.S.C. 154(b) by 1188 days.

(21) Appl. No.: 10/546,226

(22) PCT Filed: Mar. 28, 2003

(86) PCT No.: PCT/CN03/00228

§ 371 (c)(1),
(2), (4) Date: Mar. 3, 2006

(87) PCT Pub. No.: WO2004/074835

PCT Pub. Date: Sep. 2, 2004

(65) Prior Publication Data

US 2006/0141610 A1    Jun. 29, 2006

(30) Foreign Application Priority Data

Feb. 20, 2003   (CN) ............................ 03 1 04663

(51) Int. Cl.
*C12M 1/34*   (2006.01)
*C12M 3/00*   (2006.01)

(52) U.S. Cl. ............... 435/287.2; 435/6; 435/288.4

(58) Field of Classification Search ............ 435/6, 435/287.2–288.5, 305.3
See application file for complete search history.

(56) References Cited

U.S. PATENT DOCUMENTS

| | | | |
|---|---|---|---|
| 6,159,727 A | 12/2000 | Bochkariov | |
| 6,258,593 B1 | 7/2001 | Schembri et al. | |
| 6,403,368 B1 | 6/2002 | Jan et al. | |
| 6,423,552 B1 * | 7/2002 | Lu et al. | 438/1 |
| 6,485,918 B1 | 11/2002 | Schermer et al. | |
| 7,332,328 B2 * | 2/2008 | Webb et al. | 435/287.2 |
| 2002/0102186 A1 | 8/2002 | McEntee et al. | |

(Continued)

FOREIGN PATENT DOCUMENTS

CN   1193049   9/1998

(Continued)

OTHER PUBLICATIONS

Supplementary European Search Report for EP 03714627.1, mailed Mar. 25, 2008, 3 pages.

(Continued)

*Primary Examiner*—Walter D Griffin
*Assistant Examiner*—Shanta G Doe
(74) *Attorney, Agent, or Firm*—Morrison & Foerster LLP (57) ABSTRACT

This invention relates generally to the field of microarray reaction devices and uses thereof. In particular, the invention provides a microarray reaction device wherein a plurality of reaction spaces are formed between a first and second plurality of projections, the heights of said plurality of reaction spaces being substantially identical and controllable by a supporting structure, and the relative positions between the first and second plurality of projections being controllable by a positioning structure. Articles of manufacture comprising the microarray reaction device and methods for assaying an analyte using the microarray reaction device are also provided.

48 Claims, 2 Drawing Sheets

U.S. PATENT DOCUMENTS

2002/0155481 A1    10/2002    Hirota et al.
2003/0157523 A1*    8/2003    Frantz et al. .................... 435/6
2004/0091939 A1*    5/2004    Cheung et al. ............... 435/7.1
2004/0126766 A1*    7/2004    Amorese ....................... 435/6

FOREIGN PATENT DOCUMENTS

| | | |
|---|---|---|
| CN | 1261669 | 8/2000 |
| CN | 1335501 | 2/2002 |
| WO | WO-01/02094 | 1/2001 |

OTHER PUBLICATIONS

Bull et al., Br. J. Cancer (2001) 84(11):1512-1519.
International Search Report for PCT/CN03/00228, mailed on Oct. 23, 2003, 3 pages.
Langan et al., (eds.) Ligand Assay, Masson Publishing Inc., New York, (1981) p. 211.
Zhu et al., Science (2001) 293:2101-2105.

* cited by examiner

MICROARRAY DEVICES HAVING CONTROLLABLE REACTION VOLUME

CROSS-REFERENCE TO RELATED APPLICATIONS

This application is the national phase of PCT application PCT/CN2003/000228 having an international filing date of Mar. 28, 2003, which claims priority from China application number 03 1 04663.0 filed Feb. 20, 2003. The contents of these documents are incorporated herein by reference.

TECHNICAL FIELD

This invention relates generally to the field of microarray reaction devices and uses thereof. In particular, the invention provides a microarray reaction device wherein a plurality of reaction spaces are formed between a first and second plurality of projections, the heights of the plurality of reaction spaces being substantially identical and controllable by a supporting structure, and the relative positions between the first and second plurality of projections being controllable by a positioning structure. Articles of manufacture comprising the microarray reaction device and methods for assaying an analyte using the microarray reaction device are also provided.

BACKGROUND ART

Microarray devices and uses thereof have become an essential part of biochemistry and molecular biology. As a high throughput detection technique, microarray devices have been widely used in biological, medical and other related fields such as life science research, drug screening, disease diagnosis, agricultural or food inspection and judicial examination, etc. (Bull et al., *Br. J Cancer,* 84(11):1512-9 (2001); and Zhu et al., *Science,* 293:2101-5 (2001)).

Microarray reactions are effected via microarray devices. The quality of the microarray devices determines not only speed and convenience of the reactions, but also the quality of the reaction results, e.g., strength of the signal, strength of the noise, signal uniformity and assay reliability.

Take a gene chip as an example, current microarray reaction devices are comprised of microarray slide, cover and hybridization cassette. The microarray slide is often the standard slide with the size of 1"×3" and the cover is often the plastic or glass plate with a thickness of 0.16 mm. The hybridization or reaction cassette is often comprised of metal, plastic or a combination thereof. Microarray reaction devices, especially the hybridization or reaction cassettes, have been improved greatly (U.S. Pat. Nos. 6,159,727 and 6,258,593). However, the microarray slide and cover can still be improved in numerous aspects including: 1) Because the standard-sized slide is used, a relatively large amount of sample is needed to cover the slide, which may result in waste of precious or expensive sample; 2) When multiple samples are analyzed on a single slide, it is easy to have cross-contamination and reduce assay reliability; 3) Without a positioning structure between the slide and the cover, the cover may slide along the surface of the slide causing unequal thickness of hybridization liquid, reducing signal uniformity and increasing noise level at certain area; and 4) When multiple samples are analyzed on a single slide, it is often necessary to seek for arrayed locations for attaching probes thereupon, rendering the operation inconvenient, reducing speed and assay reliability.

When multiple samples are analyzed on a single slide, the use of grille adhered closely to the surface of the chip has been suggested (CN 1261669). This design may render the operation more convenient, but it still does not address the assay consistency and stability.

The present invention addresses the above and other related concerns in the art.

DISCLOSURE OF THE INVENTION

In one aspect, the present invention is directed to a microarray reaction device, which device comprises: a) a microarray chip comprising a first plurality of projections; b) a cover comprising a second plurality of projections; c) a supporting structure on said microarray chip and/or said cover; and d) a positioning structure on said microarray chip and/or said cover, wherein a plurality of reaction spaces are formed between at least some first projections and at least some second projections, the heights of said plurality of reaction spaces being substantially identical and controllable by the height of said supporting structure, and the relative positions between said first plurality of projections and said second plurality of projections being controllable by said positioning structure.

In another aspect, the present invention is directed to an article of manufacture, which article of manufacture comprises: a) packaging material; b) an above-described microarray reaction device; and c) a label indicating that the article is for assaying an analyte.

In still another aspect, the present invention is directed to a method for assaying an analyte, which method comprises: a) providing an above-described microarray reaction device; b) attaching a plurality of reactants to said first and/or said second plurality of projections of said microarray reaction device provided in a), wherein at least one of said reactants is capable of binding to an analyte to be analyzed; c) contacting a sample suspected of containing said analyte with said reactant(s) provided in step a) under suitable conditions to allow binding of said analyte, if present in said sample, to said reactant(s); and d) assessing binding between said analyte to said reactant(s) to determine presence and/or amount of said analyte in said sample.

In yet another aspect, the present invention is directed to a kit for assaying an analyte, which kit comprises: a) an above-described microarray reaction device; b) means for attaching a plurality of reactants to said first and/or said second plurality of projections of said microarray reaction device provided in a), wherein at least one of said reactants is capable of binding to an analyte to be analyzed; and c) means for assessing binding between said analyte to said reactant(s) to determine presence and/or amount of said analyte in said sample.

MODES OF CARRYING OUT THE INVENTION

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "microarray chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces.

As used herein, "microlocations" refers to places that are within, on the surface or attached to the substrate wherein the microarray chips and/or other structures or devices are located.

As used herein, "distinct microlocations" means that the microlocations are sufficiently separated so that, if needed, reagents can be added and/or withdrawn and reactions can be conducted in one microlocation independently from another microlocation. It is not necessary that each microlocation is "distinct" from all other microlocations, although in certain embodiments, each microlocation can be "distinct" from all other microlocations.

As used herein, "microlocations are in a well format" means that there are indentations with suitable three dimensional shape at the microlocations so that microarray chips and/or other structures or devices such as temperature controllers, can be built or placed into.

As used herein, "microlocations is thermally insulated" means that the microlocations have certain structures or substances that can be used to adjust to and maintain temperature at a microlocation at a desired level independently from other microlocations or any place outside the microlocation.

As used herein, "the heights of said plurality of reaction spaces being substantially identical" means that the differences among the heights of said plurality of reaction spaces are sufficiently small not to statistically affect assay uniformity. Normally, the difference between the highest height and the lowest height is less than 50% of the highest height of the reaction space. Preferably, the difference between the highest height and the lowest height is less than 40%, 30%, 20%, 10%, 5%, 2%, 1% or less than 1% of the highest height of the reaction space.

As used herein, "a group of structurally and/or functionally related proteins" refers to a group of proteins, at their natural status, that are structurally linked, located at the same cellular locations, e.g., cellular organelles, located in the same tissues or organs, expressed and/or be functional in the same biological stages, e.g., a particular cell cycle stage or developmental stage, or expressed and/or be functional in the same biological pathway, e.g., a particular metabolism pathway, signal transduction pathway, etc. The "group of structurally and/or functionally related proteins" need only include at least two proteins belonging to the same group. The "group of structurally and/or functionally related proteins" can preferably include more than two proteins belonging to the same group, e.g., a majority of or even all the proteins belonging to the same group.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein: "stringency of hybridization" in determining percentage mismatch is as follows:

1) high stringency: 0.1×SSPE, 0.1% SDS, 65° C.;
2) medium stringency: 0.2×SSPE, 0.1% SDS, 50° C. (also referred to as moderate stringency); and
3) low stringency: 1.0×SSPE, 0.1% SDS, 50° C.

It is understood that equivalent stringencies may be achieved using alternative buffers, salts and temperatures.

As used herein, "gene" refers to the unit of inheritance that occupies a specific locus on a chromosome, the existence of which can be confirmed by the occurrence of different allelic forms. Given the occurrence of split genes, gene also encompasses the set of DNA sequences (exons) that are required to produce a single polypeptide.

As used herein, "gene chip" refers to an array of oligonucleotides immobilized on a surface that can be used to screen an RNA sample (after reverse transcription) and thus a method for rapidly determining which genes are being expressed in the cell or tissue from which the RNA came.

As used herein, "specific binding" refers to the binding of one material to another in a manner dependent upon the presence of a particular molecular structure. For example, a receptor will selectively bind ligands that contain the chemical structures complementary to the ligand binding site(s).

As used herein, "specific binding pair" refers to any substance, or class of substances, which has a specific binding affinity for the ligand to the exclusion of other substances. In one embodiment, the specific binding pair includes specific binding assay reagents which interact with the sample ligand or the binding capacity of the sample for the ligand in an immunochemical manner. For example, there will be an antigen-antibody or hapten-antibody relationship between reagents and/or the sample ligand or the binding capacity of the sample for the ligand. Additionally, it is well understood in the art that other binding interactions between the ligand and the binding partner serve as the basis of specific binding assays, including the binding interactions between hormones, vitamins, metabolites, and pharmacological agents, and their respective receptors and binding substances. (See e.g., Langan et al. eds., *Ligand Assay*, pp. 211 et seq., Masson Publishing U.S.A. Inc., New York, 1981).

As used herein, "antibody" refers to specific types of immunoglobulin, i.e., IgA, IgD, IgE, IgG, e.g., $IgG_1$, $IgG_2$, $IgG_3$, and $IgG_4$, and IgM. An antibody can exist in any suitable form and also encompass any suitable fragments or derivatives. Exemplary antibodies include a polyclonal antibody, a monoclonal antibody, a Fab fragment, a Fab' fragment, a $F(ab')_2$ fragment, a Fv fragment, a diabody, a single-chain antibody and a multi-specific antibody formed from antibody fragments.

As used herein, "sample" refers to anything which may contain a target cell, cellular organelle or virus to be separated or isolated using the present methods and/or kits. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). Biological tissues may be processed to obtain cell suspension samples. The sample may also be a mixture of cells prepared in vitro. The sample may also be a cultured cell suspension. In case of the biological samples, the sample may be crude samples or processed samples that are obtained after various processing or preparation on the original samples. For example, various cell separation methods (e.g., magnetically activated cell sorting) may be applied to separate or enrich target cells from a body fluid sample such as blood. Samples used for the present invention include such target-cell enriched cell preparation.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "moiety" encompasses both test moiety and target moiety. Non-limiting examples of moieties include cells, cellular organelles, viruses, particles, molecules, e.g., proteins, DNAs and RNAs, or an aggregate or complex thereof.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

B. Microarray Reaction Devices and Article of Manufactures

In one aspect, the present invention is directed to a microarray reaction device, which device comprises: a) a microarray chip comprising a first plurality of projections; b) a cover comprising a second plurality of projections; c) a supporting structure on said microarray chip and/or said cover; and d) a positioning structure on said microarray chip and/or said cover, wherein a plurality of reaction spaces are formed between at least some first projections and at least some second projections, the heights of said plurality of reaction spaces being substantially identical and controllable by the height of said supporting structure, and the relative positions between said first plurality of projections and said second plurality of projections being controllable by said positioning structure.

The microarray chip and/or the cover can comprise any suitable material. For example, the microarray chip and/or the cover can comprise a material selected from the group consisting of a silicon, a plastic, a glass, a ceramic, a rubber, a metal, a polymer and a combination thereof.

The surface of the first plurality of projections and/or the second plurality of projections can comprise any suitable material. For example, the surface of the first plurality of projections and/or the second plurality of projections comprises a material selected from the group consisting of a silicon, a plastic, a glass, a ceramic, a rubber, a metal, a polymer and a combination thereof.

The surface of the first plurality of projections and/or the second plurality of projections can be hydrophobic or hydrophilic.

The surface of the first plurality of projections and/or the second plurality of projections can have any suitable shape. For example, the surface of the first plurality of projections and/or the second plurality of projections can have a shape selected from the group consisting of a square, a rectangle, a circle, an ellipse, an oval and an irregular shape.

The first plurality of projections and/or the second plurality of projections can have any suitable thickness. For example, the thickness of the first plurality of projections and/or the second plurality of projections can range from about 0.1 mm to about 2 mm.

The surface of the first plurality of projections and/or the second plurality of projections can have any suitable surface area. For example, the surface of the first plurality of projections and/or the second plurality of projections can have an area ranging from about 1 $mm^2$ to about 600 $mm^2$.

The present microarray reaction device can have any suitable number of the first plurality of projections and/or the second plurality of projections. For example, the number of the first plurality of projections and/or the second plurality of projections can range from about 2 to about 2,500. Preferably, a plurality of reaction spaces are formed between all first projections on the microarray chip and all second projections on the cover.

The first plurality of projections can have identical or different shape(s) and/or surface area(s). The second plurality of projections can have identical or different shape(s) and/or surface area(s). Preferably, the present microarray reaction device has identical or different number of first and second plurality of projections. Also preferably, the first plurality of projections and the second plurality of projections have identical or different shape(s) and/or surface area(s). Also preferably, the first plurality of projections and/or the second plurality of projections comprise arrayed locations for attaching probes thereupon.

The supporting structure and/or the positioning structure can comprise any suitable material. For example, the supporting structure and/or the positioning structure can comprise a material selected from the group consisting of a silicon; a plastic, a glass, a ceramic, a rubber, a metal, a polymer and a combination thereof.

The supporting structure and the positioning structure can have any suitable locations. For example, the supporting structure can be located on the microarray chip or on the cover. Similarly, the positioning structure can be located on the microarray chip or on the cover. The positioning structure can further comprise a sealing ring.

The microarray chip, the first plurality of projections, the cover, the second plurality of projections, the supporting structure and/or the positioning structure can be made by any suitable method. For example, the microarray chip, the first plurality of projections, the cover, the second plurality of projections, the supporting structure and/or the positioning structure can be made by a method selected from the group consisting of molding, gluing, dicing/cutting, slicing, anodic bonding, ultrasonic welding, electric discharge machining (EDM) wire cutting and a combination thereof.

The plurality of reaction spaces can have any suitable height. For example, the plurality of reaction spaces can have a height ranging from about 0.01 mm to about 1 mm. The plurality of reaction spaces have any suitable volume. For example, the plurality of reaction spaces can have a volume ranging from about 0.01 mm$^3$ to about 600 mm$^3$. Preferably, the plurality of reaction spaces are spatially separated from each other to avoid cross contamination.

In another aspect, the present invention is directed to an article of manufacture, which article of manufacture comprises: a) packaging material; b) an above-described microarray reaction device; and c) a label indicating that the article is for assaying an analyte.

C. Methods and Kits for Assaying an Analyte

In still another aspect, the present invention is directed to a method for assaying an analyte, which method comprises: a) providing an above-described microarray reaction device; b) attaching a plurality of reactants to said first and/or said second plurality of projections of said microarray reaction device provided in a), wherein at least one of said reactants is capable of binding to an analyte to be analyzed; c) contacting a sample suspected of containing said analyte with said reactant(s) provided in step a) under suitable conditions to allow binding of said analyte, if present in said sample, to said reactant(s); and d) assessing binding between said analyte to said reactant(s) to determine presence and/or amount of said analyte in said sample.

The present method can be used to assay any analyte, e.g., a cell, a cellular organelle, a virus, a molecule and an aggregate or complex thereof. Exemplary cells include animal cells, plant cells, fungus cells, bacterium cells, recombinant cells and cultured cells. Animal, plant, fungus, bacterium cells can be derived from any genus or subgenus of the Animalia, Plantae, fungus or bacterium kingdom. Cells derived from any genus or subgenus of ciliates, cellular slime molds, flagellates and microsporidia can also be assayed by the present methods. Cells derived from birds such as chickens, vertebrates such as fish and mammals such as mice, rats, rabbits, cats, dogs, pigs, cows, ox, sheep, goats, horses, monkeys and other non-human primates, and humans can be assayed by the present methods.

For animal cells, cells derived from a particular tissue or organ can be assayed by the present methods. For example, connective, epithelium, muscle or nerve tissue cells can be assayed. Similarly, cells derived from an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be used. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be assayed. Further, cells derived from any plants, fungi such as yeasts, bacteria such as eubacteria or archaebacteria can be assayed. Recombinant cells derived from any eucaryotic or prokaryotic sources such as animal, plant, fungus or bacterium cells can also be assayed. Body fluid such as blood, urine, saliva, bone marrow, sperm or other ascitic fluids, and subfractions thereof, e.g., serum or plasma, can also be assayed.

Exemplary cellular organelles include nuclei, mitochondria, chloroplasts, ribosomes, ERs, Golgi apparatuses, lysosomes, proteasomes, secretory vesicles, vacuoles and microsomes. Exemplary molecules include inorganic molecules, organic molecules and a complex thereof. Exemplary organic molecules include amino acids, peptides, proteins, nucleosides, nucleotides, oligonucleotides, nucleic acids, vitamins, monosaccharides, oligosaccharides, carbohydrates, lipids and a complex thereof.

Any amino acids can be assayed by the present methods. For example, a D- and a L-amino-acid can be assayed. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be assayed by the present methods.

Any proteins or peptides can be assayed by the present methods. For example, enzymes, transport proteins such as ion channels and pumps, nutrient or storage proteins, contractile or motile proteins such as actins and myosins, structural proteins, defense protein or regulatory proteins such as antibodies, hormones and growth factors can be assayed. Proteineous or peptidic antigens can also be assayed.

Any nucleic acids, including single-, double and triple-stranded nucleic acids, can be assayed by the present methods. Examples of such nucleic acids include DNA, such as A-, B- or Z-form DNA, and RNA such as mRNA, tRNA and rRNA.

Any nucleosides can be assayed by the present methods. Examples of such nucleosides include adenosine, guanosine, cytidine, thymidine and uridine. Any nucleotides can be assayed by the present methods. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any vitamins can be assayed by the present methods. For example, water-soluble vitamins such as thiamine, riboflavin, nicotinic acid, pantothenic acid, pyridoxine, biotin, folate, vitamin $B_{12}$ and ascorbic acid can be assayed. Similarly, fat-soluble vitamins such as vitamin A, vitamin D, vitamin E, and vitamin K can be assayed.

Any monosaccharides, whether D- or L-monosaccharides and whether aldoses or ketoses, can be assayed by the present methods. Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be assayed by the present methods. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

The present method can be used to assay any sample. For example, the present method can be used to assay a mammalian sample. Exemplary mammals include bovines, goats, sheep, equines, rabbits, guinea pigs, murine, humans, felines, monkeys, dogs and porcines. The present method can also be used to assay a clinical sample. Exemplary clinical samples include serum, plasma, whole blood, sputum, cerebral spinal fluid, amniotic fluid, urine, gastrointestinal contents, hair, saliva, sweat, gum scrapings and tissue from biopsies. Preferably, the present method can be used to assay a human clinical sample.

Any suitable reactant(s) can be used in the present methods. Preferably, the reactant(s) used in the present methods binds specifically with the analyte. Exemplary reactants include cells, cellular organelles, viruses, molecules and an aggregate or complex thereof Preferably, the reactant is an antibody. Also preferably, the reactant is a nucleic acid.

The present methods can be used in any suitable assay format. For example, the present methods can be used in a direct assay format, a sandwich assay format or a competition assay format.

In one embodiment, a different plurality of reactants are used to assay a single analyte. In another embodiment, a different plurality of reactants are used to assay a different plurality of analytes. In still another embodiment, a plurality of reactants are attached to the first plurality of projections of the microarray. In yet another embodiment, all reactants are capable of binding to an analyte to be analyzed.

In yet another aspect, the present invention is directed to a kit for assaying an analyte, which kit comprises: a) an above-described microarray reaction device; b) means for attaching a plurality of reactants to said first and/or said second plurality of projections of said microarray reaction device provided in a), wherein at least one of said reactants is capable of binding to an analyte to be analyzed; and c) means for assessing binding between said analyte to said reactant(s) to determine presence and/or amount of said analyte in said sample.

The kit can further comprise a plurality of reactants, wherein at least one of the reactants is capable of binding to an analyte to be analyzed. The kit can also further comprise an instruction for using the kit to assay the analyte.

The present methods and kits can be used to detect any interaction(s) among moieties selected from the group consisting of a cell, a cellular organelle, a virus, a molecule and an aggregate or complex thereof. For example, the present methods and kits can be used to detect interactions between or among macromolecules, such as DNA-DNA, DNA-RNA, RNA-RNA, DNA-protein, RNA-protein and protein-protein, etc., interactions. The present methods and kits can also be used to detect macromolecule-small molecule or small molecule-small molecule interactions. The present methods and kits can also be used to detect more complex interactions including interactions among more than two moieties. When DNA-DNA, DNA-RNA, RNA-RNA interactions are to be detected, the contacting, i.e., hybridizing, step, can be conducted under suitable condition, e.g., under low, middle or high stringency.

The interaction between said test moiety and said plurality of target moieties can be detected by any suitable methods. For example, the test moiety and/or target moieties can be labeled to facilitate detection. Any suitable label can be used. Exemplary labels include a radioactive, a fluorescent, a chemical, an enzymatic, a luminescent and a FRET (fluorescence resonance energy transfer) label. The luminescent label can be a chemiluminescent label or a bioluminescent label. The labels can be attached or conjugated, directly or indirectly, to the test moiety alone, the target moiety alone, or on both. The read-out can be a positive or a negative signal. Any suitable assay formats, including sandwich or competitive formats, can be used.

In a preferred embodiment, the present methods and kits are used to detect interaction between or among a test moiety and a plurality of genes, gene fragments or their encoded products. More preferably, the plurality of target genes, gene fragments or their encoded products are involved in a biological pathway, belong to a group of proteins with identical or similar biological function, expressed in a stage of cell cycle, expressed in a cell type, expressed in a tissue type, expressed in an organ type, expressed in a developmental stage, proteins whose expression and/or activity is altered in a disease or disorder type or stage, or proteins whose expression and/or activity is altered by drug or other treatments.

The present methods and kits can be used in detecting interaction between or among a single test moiety or substance and a plurality of target moieties. Preferably, the present methods are used in high-throughput mode, i.e., in detecting interaction between or among a plurality of test moieties or substances and a plurality of target moieties. The interaction between a plurality of test moieties or substances and a plurality of target moieties can be detected simultaneously or sequentially.

D. Exemplary Embodiments

One objective of certain preferred embodiments of the present invention is to address shortcomings of currently available microarray reaction devices. Another objective of certain preferred embodiments of the present invention is to provide a user with a convenient, fast and reliable microarray reaction device.

To achieve the above objectives, the preferred embodiments of the present invention is directed to a microarray reaction device, which device comprises: a) a microarray chip comprising a first plurality of projections; b) a cover comprising a second plurality of projections; c) a supporting structure on said microarray chip and/or said cover; and d) a positioning structure on said microarray chip and/or said cover, wherein a plurality of reaction spaces are formed between at least some first projections and at least some second projections, the heights of said plurality of reaction spaces being substantially identical and controllable by the height of said supporting structure, and the relative positions between said first plurality of projections and said second plurality of projections being controllable by said positioning structure.

The first plurality of projections and/or the second plurality of projections of the microarray reaction device can further comprise arrayed locations for attaching probes thereupon. The plurality of reaction spaces in the microarray reaction device can have a height ranging from about 0.01 mm to about 1 mm. The surface of the first plurality of projections and/or the second plurality of projections can have a shape selected from the group consisting of a square, a rectangle, a circle, an ellipse, an oval and an irregular shape. The surface of the first plurality of projections and/or the second plurality of projections can have an area ranging from about 1 mm$^2$ to about 600 mm$^2$. The first plurality of projections and the second plurality of projections can have identical or different shape(s) and/or surface area(s).

The exemplary microarray reaction devices can be used in assaying the interaction between nucleic acids, immunoreactions involving proteins, interactions between a protein and a nucleic acid, a ligand-receptor interaction, and small molecule and protein or nucleic acid interactions.

The microarray chip, the cover, the surface of the first plurality of projections and/or the second plurality of projections can comprise a material selected from the group consisting of a silicon, a plastic, a glass, a ceramic, a rubber, a metal, a polymer and a combination thereof. The microarray chip, the first plurality of projections, the cover, the second plurality of projections, the supporting structure and/or the positioning structure can be made by a method selected from the group consisting of molding, gluing, dicing/cutting, slicing, anodic bonding, ultrasonic welding, EDM wire cutting and a combination thereof.

The exemplary microarray reaction devices have the following advantages: 1) due to the use of the first multiple projections with small surface areas, less sample volume is required leading to cost saving; 2) the use of the positioning structure ensures control of the relative positions between the plurality of projections and consequently, homogeneity of the thickness or volume of the reaction, e.g., hybridization, liquid; 3) when multiple samples are assayed, the existence of the multiple reaction, e.g., hybridization, spaces reduces cross contamination and ensures assay reliability; 4) due to the use of the positioning structure, it is not necessary to search for the positions for arrayed locations for attaching probes, thus making the operation more convenient and at the same time increasing assay reliability.

The exemplary microarray reaction devices can be used in disease prognosis or diagnosis, life science research, agriculture and environment monitoring, food and hygiene inspection and judicial examination. In particular, the exemplary microarray reaction devices can be used with minimal cross contamination. Therefore, the exemplary microarray reaction devices are particularly suited for simultaneous assay of multiple samples and are useful in various prognosis or diagnosis, e.g., simultaneous assay of multiple markers, multiple diseases and/or for multiple patients.

As seen in FIGS. 1-5, the exemplary microarray reaction devices can comprise a microarray chip (1), a cover (2), a supporting structure (3) and reaction space(s). The reaction space(s) can comprise a positioning structure (4), a sealing ring (5) and a pressuring cover, etc. The microarray chip (1) is used for sample application. The microarray chip (1), the cover (2), the supporting structure (3) and the positioning structure (4) collectively form the reaction space(s).

The microarray chip (1) can have two or more projections (6). The cover (2) can have the same number of projections (7). The supporting structure (3) and the positioning structure (4) can be used to control the relative positions between the plurality of projections on the microarray chip (1) and the cover (2) to form the numerous reaction spaces (8) with controllable thickness or volume. Same reactions can be carried out in the multiple reaction spaces to assess assay reliability. Different reactions can be carried out in the multiple reaction spaces to assay multiple samples or markers simultaneously. Sufficient distance or space should be allowed among different reaction spaces to minimize cross contamination and to increase assay accuracy.

Figure 1:
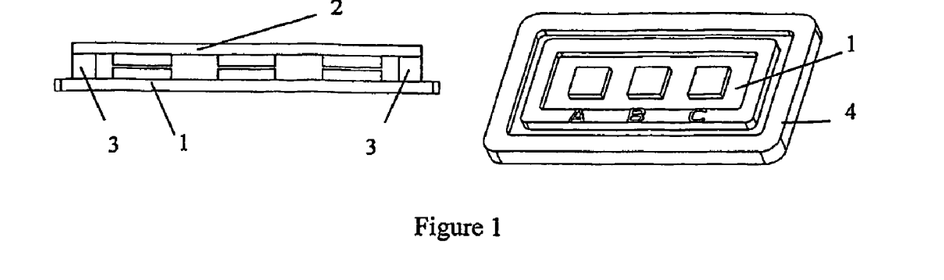
FIG. 1 illustrates various components of an exemplary microarray reaction device.
Figure 3:
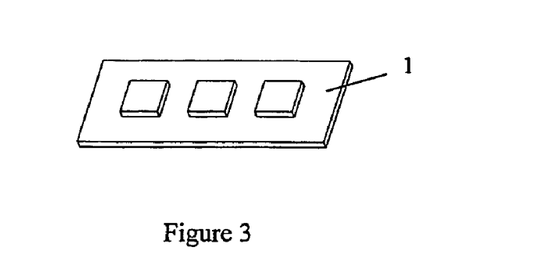
FIG. 3 is a three-dimensional illustration of the microarray chip as illustrated in FIG. 1.

The microarray chip can comprise a material selected from the group consisting of a silicon, a plastic, a glass, a ceramic, a rubber, a metal, a polymer and a combination thereof. The microarray chip, can be formed by a method selected from the group consisting of molding, gluing, dicing/cutting, slicing, anodic bonding, ultrasonic welding, EDM wire cutting and a combination thereof. For example, the base and the projections of the microarray chip can both be glass and can be glued together. Special gluing device can be used to increase gluing efficiency. To ensure gluing durability, a special ultraviolet adhesive, which can endure water, steam, $K_2CrO_4$/$H_2SO_4$ and other organic solvents, can be used. The projections (6) on microarray chip (1) can be used for sample application and have a shape selected from the group consisting of a square, a rectangle, a circle, an ellipse, an oval and an irregular shape. The surface of the projections can have an area ranging from about 1 mm$^2$ to about 600 mm$^2$.

Figure 2:
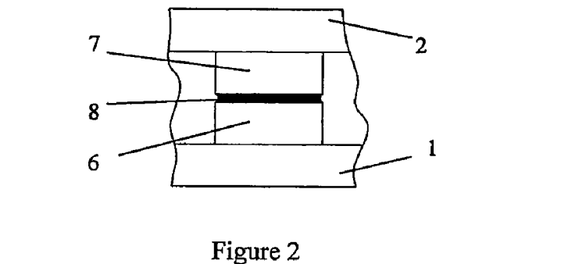
FIG. 2 illustrates the reaction spaces formed between a plurality of projections on a microarray chip and a plurality of projections on a cover slip.
Figure 4:
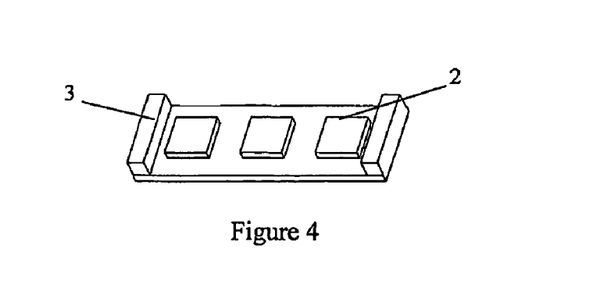
FIG. 4 is a three-dimensional illustration of an exemplary supporting structure on a cover slip as illustrated in FIG. 1.

Cover (2) can be made using the same materials and methods for making the microarray chip (1). Cover (2) can provide another set of multiple projections to form reaction spaces (8) with the projections provided on the microarray chip (1). In addition, the supporting structure can be used to control the heights of the plurality of reaction spaces.

Figure 5:
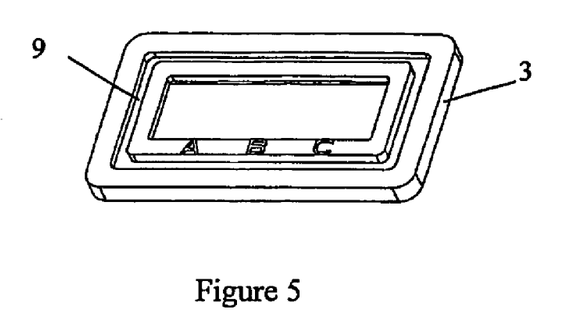
FIG. 5 is a three-dimensional illustration of an exemplary positioning structure as illustrated in FIG. 1.

The positioning structure is preferably made of plastic, and preferably by molding. The positioning structure can be used to control the relative positions between projections on the microarray chip and the cover to accurately form the reaction spaces. The positioning structure can further comprise a circular groove (9) compatible to the sealing ring (5). The sealing ring is preferably made of air-tight soft material, e.g., rubber.

Figure 6:
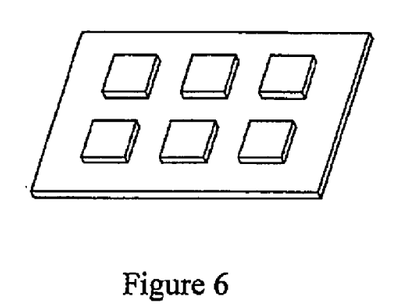
FIG. 6 is a three-dimensional illustration of an exemplary microarray chip having 2×3 projections.

FIG. 6 illustrates a microarray reaction device with a microarray chip having a 2×3 projections. The device can be used to assay two samples and each sample can be assayed three times.

The exemplary microarray reaction device illustrated in FIG. 6 can be used in assaying the interaction between nucleic acids, immunoreactions involving proteins, interactions between a protein and a nucleic acid, a ligand-receptor interaction, and small molecule and protein or nucleic acid interactions. The device can endure a reaction temperature up to 80° C. The device can also endure liquid washing.

Figure 7:
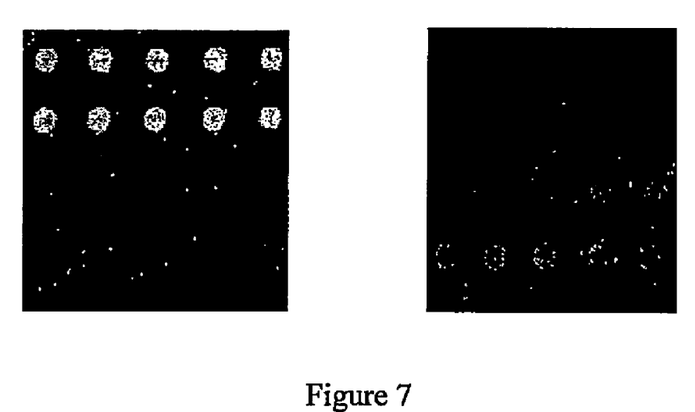
FIG. 7 shows fluorescent scanning result of an analysis of two different samples using an exemplary microarray reaction device.

The reactions between sample A with probes on projection A and reactions between sample B with probes on projection B are illustrated in FIG. 7. The probes within each set of projections are identical. A probe capable of hybridizing with nucleic acid in sample A is attached to each of the projections A (the first two rows, 10 parallel positions in total). A probe capable of hybridizing with nucleic acid in sample B is attached to each of the projections B (the third and fourth rows, 10 parallel positions in total). The reactions were conducted at 65° C. for 1 hour. The sample nucleic acid s were labeled with the fluorescent dye Cy5. The Cy5 dye can be excited by a scanner at 635 nm to give a fluorescence at 675 nm, which is in direct proportional to the target nucleic acids in the samples. The scanning parameters were: laser, 80%; photomultiplier tube, 80%; and detection limit, 10 μm. FIG. 7A shows fluorescent scanning spectrum after reaction of sample A with probes on projections A. Only first and second rows have detectable signals. FIG. 7B shows fluorescent scanning spectrum after reaction of sample B with probes on projections B. Only third and fourth rows have detectable signals. These results indicate that the signals are homogeneous and there were no cross contamination.

The following illustrates an exemplary operation procedure using the exemplary device: 1) determining probe positions on each of the projections according to the samples to be assayed, and attaching the probes to the predetermined locations using a suitable sample application device; 2) applying same or different samples on the projections; 3) applying and closing the cover to allow reactions to proceed; and 4) washing the cover after the reactions are finished and analyzing the microarray chip with a fluorescent scanner.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A microarray reaction device, which device comprises:
   a) a microarray chip comprising a first plurality of projections;
   b) a cover comprising a second plurality of projections;
   c) a supporting structure on said microarray chip and/or said cover; and
   d) a positioning structure on said microarray chip and/or said cover,
   wherein a plurality of reaction spaces are formed between at least some first projections and at least some second projections, the heights of said plurality of reaction spaces being substantially identical and controllable by the height of said supporting structure, and the relative positions between said first plurality of projections and said second plurality of projections being controllable by said positioning structure.

2. The microarray reaction device of claim 1, wherein the microarray chip and/or the cover comprises a material selected from the group consisting of a silicon, a plastic, a glass, a ceramic, a rubber, a metal, a polymer and a combination thereof.

3. The microarray reaction device of claim 1, wherein the surface of the first plurality of projections and/or the second plurality of projections comprises a material selected from the group consisting of a silicon, a plastic, a glass, a ceramic, a rubber, a metal, a polymer and a combination thereof.

4. The microarray reaction device of claim 1, wherein the surface of the first plurality of projections and/or the second plurality of projections is hydrophobic or hydrophilic.

5. The microarray reaction device of claim 1, wherein the surface of the first plurality of projections and/or the second plurality of projections has a shape selected from the group consisting of a square, a rectangle, a circle, an ellipse, an oval and an irregular shape.

6. The microarray reaction device of claim 1, wherein the thickness of the first plurality of projections and/or the second plurality of projections ranges from about 0.1 mm to about 2 mm.

7. The microarray reaction device of claim 1, wherein the surface of the first plurality of projections and/or the second plurality of projections has an area ranging from about 1 $mm^2$ to about 600 $mm^2$.

8. The microarray reaction device of claim 1, wherein the number of the first plurality of projections and/or the second plurality of projections ranges from about 2 to about 2,500.

9. The microarray reaction device of claim 1, wherein the first plurality of projections have identical or different shape(s) and/or surface area(s).

10. The microarray reaction device of claim 1, wherein the second plurality of projections have identical or different shape(s) and/or surface area(s).

11. The microarray reaction device of claim 1, which has identical or different number of first and second plurality of projections.

12. The microarray reaction device of claim 1, wherein the first plurality of projections and the second plurality of projections have identical or different shape(s) and/or surface area(s).

13. The microarray reaction device of claim 1, wherein the first plurality of projections and/or the second plurality of projections comprise arrayed locations for attaching probes thereupon.

14. The microarray reaction device of claim 1, wherein the supporting structure and/or the positioning structure comprises a material selected from the group consisting of a silicon, a plastic, a glass, a ceramic, a rubber, a metal, a polymer and a combination thereof.

15. The microarray reaction device of claim 1, wherein the supporting structure is located on the microarray chip.

16. The microarray reaction device of claim 1, wherein the supporting structure is located on the cover.

17. The microarray reaction device of claim 1, wherein the positioning structure is located on the microarray chip.

18. The microarray reaction device of claim 1, wherein the positioning structure is located on the cover.

19. The microarray reaction device of claim 1, wherein the positioning structure further comprises a sealing ring.

20. The microarray reaction device of claim 1, wherein the microarray chip, the first plurality of projections, the cover, the second plurality of projections, the supporting structure and/or the positioning structure is made by a method selected from the group consisting of molding, gluing, dicing/cutting, slicing, anodic bonding, ultrasonic welding, EDM wire cutting and a combination thereof.

21. The microarray reaction device of claim 1, wherein a plurality of reaction spaces are formed between all first projections on the microarray chip and all second projections on the cover.

22. The microarray reaction device of claim 1, wherein the plurality of reaction spaces have a height ranging from about 0.01 mm to about 1 mm.

23. The microarray reaction device of claim 1, wherein the plurality of reaction spaces have a volume ranging from about 0.01 $mm^3$ to about 600 $mm^3$.

24. The microarray reaction device of claim 1, wherein the plurality of reaction spaces are spatially separated from each other to avoid cross contamination.

25. An article of manufacture, which article of manufacture comprises:
   a) packaging material;
   b) a microarray reaction device of claim 1; and c) a label indicating that the article is for assaying an analyte.

26. A method for assaying an analyte, which method comprises:
   a) providing a microarray reaction device of claim 1;
   b) attaching a plurality of reactants to said first and/or said second plurality of projections of said microarray reaction device provided in a), wherein at least one of said reactants is capable of binding to an analyte to be analyzed;
   c) contacting a sample suspected of containing said analyte with said reactant(s) provided in step a) under suitable conditions to allow binding of said analyte, if present in said sample, to said reactant(s); and
   d) assessing binding between said analyte to said reactant(s) to determine presence and/or amount of said analyte in said sample.

27. The method of claim 26, wherein the analyte is selected from the group consisting of a cell, a cellular organelle, a virus, a molecule and an aggregate or complex thereof.

28. The method of claim 27, wherein the cell is selected from the group consisting of an animal cell, a plant cell, a fungus cell, a bacterium cell, a recombinant cell and a cultured cell.

29. The method of claim 27, wherein the cellular organelle is selected from the group consisting of a nuclei, a mitochondrion, a chloroplast, a ribosome, an ER, a Golgi apparatus, a lysosome, a proteasome, a secretory vesicle, a vacuole and a microsome.

30. The method of claim 27, wherein the molecule is selected from the group consisting of an inorganic molecule, an organic molecule and a complex thereof.

31. The method of claim 30, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

32. The method of claim 26, wherein the sample is a mammalian sample.

33. The method of claim 32, wherein the mammal is selected from the group consisting of bovine, goat, sheep, equine, rabbit, guinea pig, murine, human, feline, monkey, dog and porcine.

34. The method of claim 26, wherein the sample is a clinical sample.

35. The method of claim 34, wherein the clinical sample is selected from the group consisting of serum, plasma, whole blood, sputum, cerebral spinal fluid, amniotic fluid, urine, gastrointestinal contents, hair, saliva, sweat, gum scrapings and tissue from biopsies.

36. The method of claim 34, wherein the clinical sample is a human clinical sample.

37. The method of claim 26, wherein the reactant(s) binds specifically with the analyte.

38. The method of claim 26, wherein the reactant is selected from the group consisting of a cell, a cellular organelle, a virus, a molecule and an aggregate or complex thereof.

39. The method of claim 26, wherein the reactant is an antibody.

40. The method of claim 26, wherein the reactant is a nucleic acid.

41. The method of claim 26, which is used in a direct assay format, a sandwich assay format or a competition assay format.

42. The method of claim 26, wherein a different plurality of reactants are used to assay a single analyte.

43. The method of claim 26, wherein a different plurality of reactants are used to assay a different plurality of analytes.

44. The method of claim 26, wherein a plurality of reactants are attached to the first plurality of projections of the microarray.

45. The method of claim 26, wherein all reactants are capable of binding to an analyte to be analyzed.

46. A kit for assaying an analyte, which kit comprises:
   a) a microarray reaction device of claim 1;
   b) means for attaching a plurality of reactants to said first and/or said second plurality of projections of said microarray reaction device provided in a), wherein at least one of said reactants is capable of binding to an analyte to be analyzed; and
   c) means for assessing binding between said analyte to said reactant(s) to determine presence and/or amount of said analyte in said sample.

47. The kit of claim 46, which further comprises a plurality of reactants, wherein at least one of the reactants is capable of binding to an analyte to be analyzed.

48. The kit of claim 46, which further comprises an instruction for using the kit to assay the analyte.

* * * * *